US006310015B1

(12) United States Patent
Diez et al.

(10) Patent No.: US 6,310,015 B1
(45) Date of Patent: Oct. 30, 2001

(54) TRANSPARENT/TRANSLUCENT MOISTURIZING/COSMETIC/PERSONAL CLEANSING BAR

(75) Inventors: Ricardo Diez, Scottsdale, AZ (US); Maria Mercedes Garcia, Guatemala City (GT)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 09/609,226

(22) Filed: Jun. 30, 2000

Related U.S. Application Data

(63) Continuation of application No. 09/497,239, filed on Feb. 3, 2000, now abandoned, which is a continuation-in-part of application No. 09/430,492, filed on Oct. 29, 1999, now abandoned, which is a continuation-in-part of application No. 09/371,431, filed on Aug. 10, 1999, now abandoned.

(51) Int. Cl.[7] ..................... A61K 7/50

(52) U.S. Cl. ..................... 510/130; 510/147; 510/152; 510/155

(58) Field of Search ..................... 510/130, 147, 510/152, 155, 426, 428, 432

(56) References Cited

U.S. PATENT DOCUMENTS

| | | | |
|---|---|---|---|
| 3,929,678 | 12/1975 | Laughlin et al. | 252/526 |
| 4,165,293 * | 8/1979 | Gordon | 510/118 |
| 4,739,007 | 4/1988 | Okada et al. | 524/789 |
| 4,810,734 | 3/1989 | Kawasumi et al. | 523/216 |
| 4,894,411 | 1/1990 | Okada et al. | 524/710 |
| 5,002,685 | 3/1991 | Chambers et al. | 252/134 |
| 5,041,234 | 8/1991 | Instone et al. | 252/118 |
| 5,496,489 | 3/1996 | Dussault et al. | 252/134 |
| 5,703,025 | 12/1997 | Zyngier et al. | 510/147 |
| 5,856,283 | 1/1999 | Abbas et al. | 510/131 |
| 5,865,283 * | 1/1999 | Abbas et al. | 510/131 |

FOREIGN PATENT DOCUMENTS

| | | |
|---|---|---|
| 0 507 559 A | 10/1992 | (EP) . |
| WO 91 16412 | 10/1991 | (WO) . |
| WO 93 04161 | 3/1993 | (WO) . |
| WO 96 04360 | 2/1996 | (WO) . |
| WO 98 14559 | 4/1998 | (WO) . |

* cited by examiner

*Primary Examiner*—Necholus Ogden
(74) *Attorney, Agent, or Firm*—Marshall, Gerstein & Borun

(57) ABSTRACT

A composition and a method of preparing a transparent/translucent moisturizing/cosmetic/personal cleansing bar having a final water content of about 13% by weight or less, preferably about 7% to about 11% water, thereby increasing the melting temperature of the bar to prevent melting and reduce deformation during storage and handling, increasing its hardness and durability, and substantially reducing the tendency of the bar to lose weight over time by evaporation of water by exposure to room temperature.

33 Claims, 1 Drawing Sheet

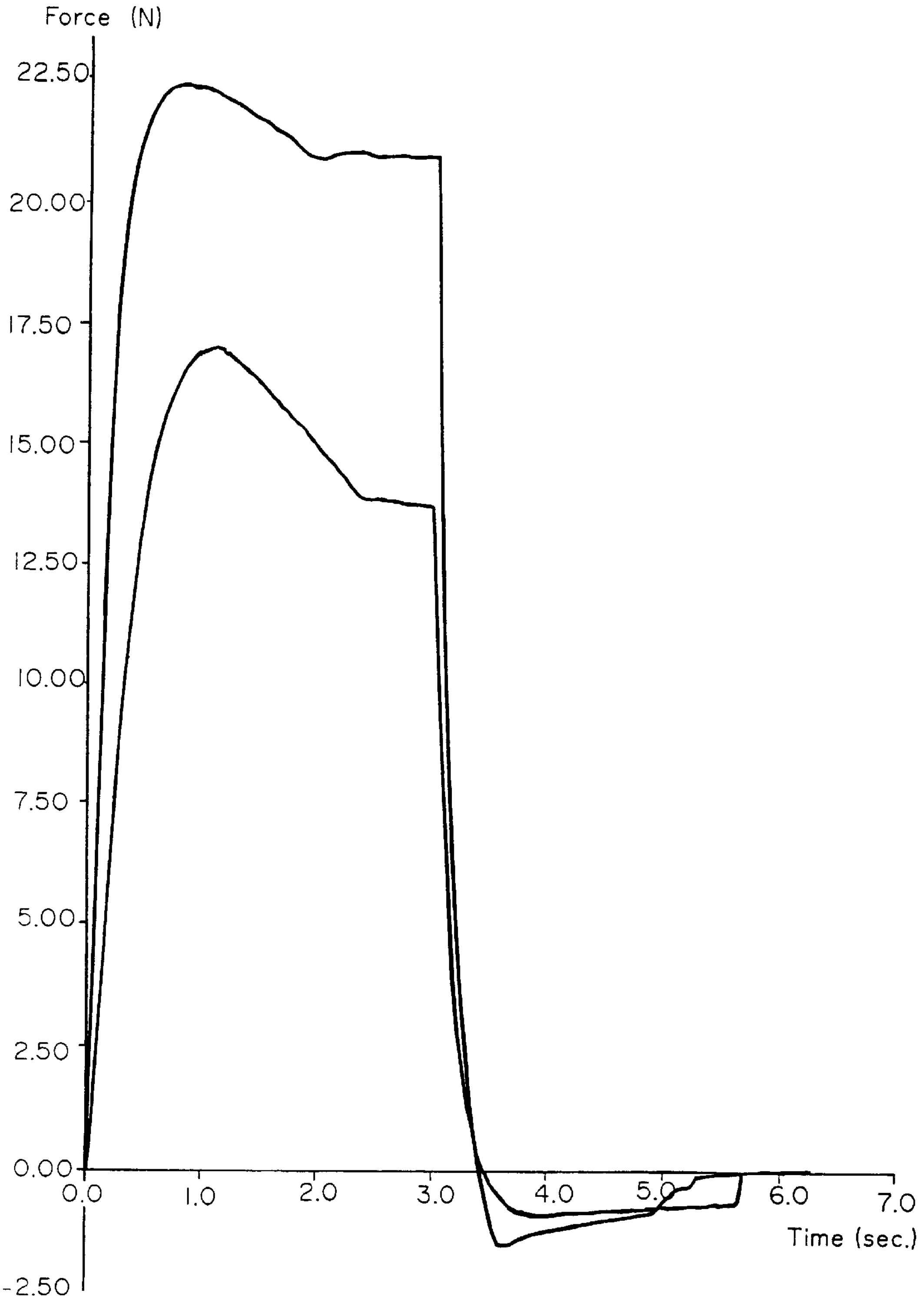
Force (N)
22.50
20.00
17.50
15.00
12.50
10.00
7.50
5.00
2.50
0.00
-2.50
0.0
1.0
2.0
3.0
4.0
5.0
6.0
7.0
Time (sec.)

TRANSPARENT/TRANSLUCENT MOISTURIZING/COSMETIC/PERSONAL CLEANSING BAR

CROSS-REFERENCE TO RELATED APPLICATION

This application is a continuation-in-part of application Ser. No. 09/497,239 filed Feb. 3, 2000 now abandoned which is a continuation-in-part of patent application Ser. No. 09/430,492 filed Oct. 29, 1999 abandoned, which is a continuation-in-part of application Ser. No. 09/371,431 filed Aug. 10, 1999 abandoned.

FIELD OF THE INVENTION

The present invention is directed to transparent/translucent moisturizing/cosmetic/personal cleansing bars (hereinafter "cleansing bars") having a melting point of at least 55° C. and increased hardness/durability, primarily due to the bars containing polyhydric solvents, in an amount of about 15% to about 65% by weight, preferably about 25% to about 65% by weight, including (A) one or more polyhydric solvents that include at least three hydroxyl groups, in an amount of 5% by weight to about 35% by weight, and (B) one or more polyhydric solvents that include two hydroxyl groups, e.g., diols or glycols, in an amount of about 10% by weight to about 30% by weight. The transparent/translucent cleansing bars contain about 4% to about 13% by weight water, preferably about 4% to about 12% water, most preferably about 7% to about 12% water. The transparent/translucent cleansing bars lose less water with time via atmospheric evaporation and have increased durability and avoid melting and deformation during shipping and handling while maintaining transparency/translucency. The bars are manufactured by forming a molten composition in liquid form, and pouring the molten composition into a mold to harden, upon cooling. The bar can be manufactured without a monohydric alcohol, or may contain a monohydric alcohol in relatively small amounts, e.g., 0.1% to 4%, preferably 0.5% to 2% by weight, for increased clarity. The bars can be manufactured to include relatively high foam, as personal cleansing/moisturizing bars, or may contain low foam surfactants as moisturizing/facial cleansing/cosmetic bars.

BACKGROUND OF THE INVENTION AND PRIOR ART

Transparent personal cleansing bars are well known in the art. They are prepared by dissolving soap in a combination of water soluble solvents (normally urea and/or polyhydric alcohols) with the addition of surfactants to improve the cleansing and lathering characteristics of the product. Water is also part of the composition and is incorporated into the bars by the direct addition of water or added from the surfactants or soap that form part of the cleansing bars.

A common problem with transparent personal cleansing bars is that they have a melting point of about 50° C., which is too close to the temperatures that are reached during shipping or storage of the products. When shipped or stored at temperatures approaching 50° C., the solid personal cleansing bars either melt or become sufficiently soft to deform. Another common problem of the personal cleansing bars is that they lose more weight than regular, opaque cleansing bars due to their relatively higher content of water, and the presence of volatile solvents, such as monohydric alcohols, e.g., ethanol.

U.S. Pat. No. 5,041,234 to Instone, et al. discloses a transparent personal cleansing bar which contains greater than 40 percent by weight of soap (high soap bar). Like other "high soap" transparent bars, the bars disclosed by Instone et al. have good lather, low smear, and good bar hardness. Such high soap level transparent bars, however, are rather harsh to the skin. Another drawback to such bars is that their processing generally require the use of at least about 5% by weight volatile, short chain monohydric alcohols, or require special milling to obtain transparency.

Transparent bars which contain lower levels of soap are also known in the art. "Lower soap" transparent bars contain less than 40 percent by weight of soap. U.S. Pat. No. 5,002,685 to Chambers et al. discloses a transparent bar made with 25% to 34% by weight soap, 5% to 15% by weight monohydric alcohol, 15% to 30% by weight sugar and/or cyclic polyol, and 15% to 30% by weight water. Unfortunately, transparent bars which require the use of at least about 5% by weight monohydric alcohols are prone to excessive weight loss due to the volatile nature of most monohydric alcohols. Such transparent bars are also more expensive to prepare and require special equipment designed to accommodate the explosion hazard associated with most monohydric alcohols.

Zyngier et al. U.S. Pat. No. 5,703,025 discloses a monohydric alcohol-free process for making pour molded transparent and translucent cleansing bars that have good hardness, are mild to the skin, low smearing and good lathering. These bars, however, require at least 14% by weight water, particularly 14% to 32% by weight water, and preferably more than 20% by weight water, so that the bars melt and deform at a relatively low temperature, e.g., about 50° C., and readily lose weight via water evaporation at room temperature and pressure. As stated in the '025 patent, "The water level within the personal cleansing bars prepared by the process of the present invention is critical to obtain a transparent bar having desirable hardness characteristics. When the water is less than about 14 parts by weight of the bar, the bar may not be transparent."

A transparent/translucent cleansing bar containing 20% by weight water loses about 17% of its original weight when exposed to room temperature for three weeks, whereas a bar containing only 10% by weight water only loses about 7.5% of its original weight under the same, standard temperature (room temperature) and pressure conditions.

SUMMARY OF THE INVENTION

In brief, the present invention is directed to a composition and a method of preparing a transparent/translucent moisturizing/cosmetic/personal cleansing bar containing polyhydric solvents, in an amount of about 15% to about 65% by weight, preferably about 25% to about 65% by weight, including one or more polyhydric solvents that include at least three hydroxyl groups, in an amount of 5% by weight to about 35% by weight, and one or more polyhydric solvents that include two hydroxyl groups, e.g., diols or glycols, in an amount of about 10% by weight to about 30% by weight. The transparent/translucent cleansing bars contain a final water content of about 13% by weight or less, preferably about 4% to about 12%, more preferably about 7% to about 12% water, thereby increasing the melting temperature of the bar to prevent melting and reduce deformation during storage and handling, increasing its hardness and durability, and substantially reducing the tendency of the bar to lose weight over time by evaporation of water by exposure to room temperature.

Accordingly, one aspect of the present invention is to provide a transparent/translucent moisturizing/cosmetic/ personal cleansing bar that is more durable, has a relatively high melting point, and a lower water content than prior art personal cleansing bars, while maintaining clarity (transparency).

Another aspect of the present invention is to provide a transparent/translucent moisturizing/cosmetic/personal cleansing bar that is less susceptible to being deformed by heat and/or pressure and includes a combination of polyhydric solvents (1) having three or more hydroxyl groups; and (2) two hydroxyl groups, while providing a bar having a minimum amount of water (4–13% by weight) so that hydrolyzable bar components, such as antibacterial components, e.g., triclocarban (TCC), maintain more of their efficacy, for longer periods of time.

BRIEF DESCRIPTION OF THE DRAWING

The FIGURE is a graph that compares the hardness, in Newtons, of the preferred bar composition of the present invention (Example 6—PREFERRED) to the same composition containing 17.7% by weight water, prior to dehydration (Example 6—FORMED).

DETAILED DESCRIPTION OF THE PREFERRED EMBODIMENTS

The transparent/translucent personal cleansing bars of the present invention include the following components, after manufacture and may contain additional additives, such as antibacterial agents, dyes, perfumes, fillers, polymers, silicones, encapsulated materials, and the like:

| | Range % | Preferred % | More Preferred % | Most Preferred % |
|---|---|---|---|---|
| water-soluble polyhydric solvent(s), | 15–65 | 25–65 | 30–55 | 35–50 |
| $3^+$-OH, e.g., glycerine, sugar alcohols, e.g., sorbitol and the like | 5–35 | 10–30 | 15–25 | 17–22 |
| 2-OH, e.g., propylene glycol, polyethylene glycol, dipropylene glycol | 10–30 | 15–30 | 20–30 | 22–27 |
| monohydric alcohol, e.g., ethanol | 0–4 | 0.5–3 | 0.5–2 | 0.75–1.5 |
| soap | 5–35 | 8–30 | 10–25 | 10–15 |
| surfactant(s) | 5–40 | 5–30 | 8–25 | 10–20 |
| water | 4–13 | 4–12 | 7–12 | 10–12 |

The term "soap", for purposes of describing this component of the transparent/translucent cleansing bar of the present invention, has the meaning as normally understood by those skilled in the art: monovalent salts of fatty monocarboxylic acids having a carbon chain length of from 12 to 24, preferably from 14 to 18 carbon atoms. These monovalent salts would normally be sodium salts, although some cations, such as K, Mg or alkanolammonium ions could be used. The preferred insoluble fatty acid soap is at least 90% by weight, more preferably at least 95% by weight selected from the group consisting of sodium myristate, sodium palmitate, sodium stearate and mixtures of any two or more thereof. Other insoluble soaps, particularly higher fatty acid insoluble soaps, can also be used.

This invention relates to the transparent cleansing/cosmetic compositions of the present invention, in a solid form, and method of manufacturing same. The transparent/translucent cosmetic/moisturizing cleansing bars of the present invention have a reduced water content, thereby increasing the melting point of the bars to at least about 60° C., preferably at least about 65° C., with reduced weight loss and increased durability and hardness.

The products of this invention can be prepared with reduced water content, for example, by using anhydrous polyhydric alcohols and/or anhydrous surfactants or by removing water from the composition initially formed with a higher water content.

Significant performance improvements are obtained by combining water-soluble polyhydric solvents having at least three hydroxyl groups ($3^+$-OH) with water-soluble polyhydric solvents having two hydroxyl groups (2-OH). Significant performance improvements also are obtained by reducing the water content to a maximum of about 13% by weight, preferably in the range of about 4% to about 12% by weight, more preferably about 7% to about 12% by weight, most preferably about 10% to about 12% by weight water. The melting point of the bar is increased to at least 55° C., which is above the temperatures that are expected to be reached during shipping and storage, thus avoiding melting and deformation of the personal cleansing bars.

Another benefit to the composition of the present invention is the reduction of weight loss. A bar containing about 20% by weight water loses about 17% of its original weight when exposed to room temperature (25° C.) for three weeks, whereas a bar with a water content of 10% by weight only loses about 7.5% of its original weight under the same conditions.

Surfactants

The bars of the present invention, include about 5% to about 40% by weight surfactants, preferably about 5% to about 30% by weight, more preferably about 8% to about 25%, most preferably about 10% to about 20% by weight surfactants.

The surfactant can be an anionic surfactant, a cationic surfactant, a nonionic surfactant, an ampholytic or amphoteric surfactant or a compatible mixture of surfactants.

Suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263–266, incorporated herein by reference. Numerous other anionic surfactants, and classes of anionic surfactants, are disclosed in Laughlin et al. U.S. Pat. No. 3,929,678, incorporated herein by reference.

The cleansing bars of the present invention also can contain nonionic surfactants. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, and mixtures thereof. Fatty alcohol ethoxylates (FAE) are preferred for dissolving antibacterial compounds, such as triclocarban (TCC).

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the *CTFA International Cosmetic Ingredient Dictionary, Fourth Ed.*, Cosmetic, Toiletry and Fragrance Association, Washington, D.C. (1991) (hereinafter the CTFA Dictionary) at pages 1–651; and in the *CTFA Handbook*, at pages 86–94, each incorporated herein by reference.

In addition to anionic and nonionic surfactants, cationic, ampholytic, and amphoteric surfactants can be used in the cleansing bars of the present invention. Cationic surfactants include amine oxides, for example.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)-propane-1-sulfonate, sodium 2-(dodecylamino)ethyl sulfate, sodium 2-(dimethylamino) octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

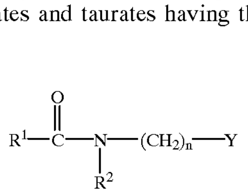

wherein $R^1$, for the above, as well as the following classes of ampholytic surfactants, is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

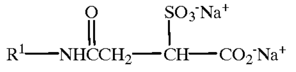

The following classes of ampholytic surfactants also can be used:

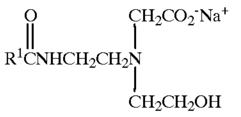

alkomphoglycinates

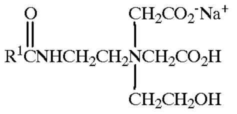

alkoamphocarboxyglycinates

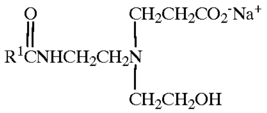

alkoamphopropionates

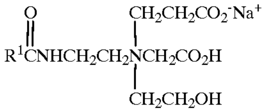

alkoamphocarboxypropionates

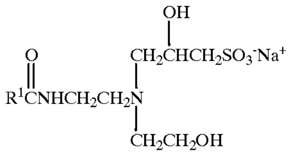

alkoamphopropylsulfonates

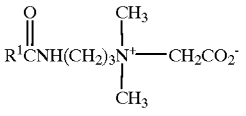

alkamidopropyl betaines

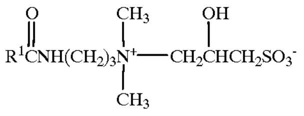

alkamidopropyl hydroxysultaine

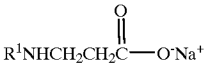

alkylaminopropionates

-continued

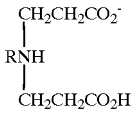

alkyliminopropionates.

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

Polyhydric Solvent(s)

The transparent bar prepared according to the process of the present invention comprises from about 15% to about 65% by weight, preferably about 25% to about 65% by weight, more preferably from about 30% to about 55% by weight, most preferably about 35% to about 50% by weight of a combination of water-soluble polyhydric organic solvents including (A) about 5% to about 35% by weight water-soluble polyhydric solvent(s) having three or more hydroxyl groups ($3^+$-OH), and (B) about 10% to about 30% by weight polyhydric solvent(s) having two hydroxyl groups (2-OH). Preferred water soluble organic polyols having two hydroxyl groups (2-OH) include those selected from the group consisting of: propylene glycol; dipropylene glycol; butylene glycol; ethylene glycol; 1,7-heptanediol; monoethylene glycols, polyethylene glycols, polypropylene glycols of up to 8,000 molecular weight; mono-$C_{1-4}$ alkyl ethers of any of the foregoing; and mixtures thereof. Preferred water-soluble polyhydric solvents that have at least three hydroxyl groups ($3^+$-OH) include glycerine, and any sugar alcohol, such as sorbitol.

Examples of suitable sugar alcohols include:

Tetritols:

Erythritol, threitol, D-threitol, L-threitol, and D,L-threitol.

Pentitols:

Ribitol, arabinitol, D-arabinitol, L-arabinitol, D,L-arabinitol and xylitol.

Hexitols:

Allitol, dulcitol (galacitol), glucitol, sorbitol, (D-glucitol), L-glucitol, D,L-glucitol, D-mannitol, L-mannitol, D,L-mannitol, altritol, D-altritol, L-altritol, D,L-altritol, iditol, D-iditol, and L-iditol.

Disaccharide alcohols:

Maltitol, lactitol and isomalt.

Soap

The fatty acid soap used in the present invention comprises sodium soaps. However, low levels of non-sodium soaps such as potassium, magnesium, and/or triethanolammonium (TEA) soaps are permissible. Such non-sodium soaps, when used, are preferably used at a level of from 0% to 10% by weight, preferably from 0% to 5% by weight of the bar soap.

Optional Ingredients

The transparent/translucent bars of the present invention also can contain optional ingredients well known to persons skilled in the art. Such optional ingredients typically are present, individually, from 0% to about 5%, by weight, of the composition, and, collectively, from 0% to about 20%, by weight, of the composition.

Suitable optional ingredients include dyes, fragrances and one or more antibacterial compounds(s), that are present in a sufficient amount to perform their intended function and do not substantially adversely affect the transparency of the composition.

Classes of optional ingredients include, but are not limited to, dyes, fragrances, pH adjusters, thickeners, fillers, viscosity modifiers, buffering agents, foam stabilizers, antioxidants, foam enhancers, chelating agents, opacifiers, sanitizing or anti-microbial agents, preservatives, polymers, silicones, encapsulated materials, and similar classes of optional ingredients known to persons skilled in the art.

Specific classes of optional ingredients include alkanolamides as foam boosters and stabilizers; gums and polymers as thickening agents; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited. and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

In accordance with a preferred embodiment of manufacturing the moisturizing/cosmetic/personal cleansing bars of the present invention, the solvents and surfactants are added in an open agitated reaction vessel at atmospheric pressure and at a temperature sufficient to melt the fatty acids, generally at least about 70° C., e.g., 70° C. to 80° C. The fatty acid(s) then are added, followed by raising the temperature to at least about 80° C., e.g., 80–90° C., prior to the addition of a neutralizing agent, preferably a sodium base, e.g., NaOH, in an amount sufficient to provide 100% neutralization of the fatty acids, to form the soap, in situ. It should be understood that the soap, i.e., sodium myristate, sodium palmitate, and/or sodium stearate, can be added in pre-manufactured form instead of being formed, in situ. At this stage of the manufacturing process, if the water content of the mixture is above 13% by weight, the temperature of the reaction mixture is raised to at least about 90° C., preferably 90° C. to 100° C. to evaporate sufficient water to provide a composition having 4–13% by weight water, most preferably about 10–12% by weight water. It should be noted that during the above-described water evaporation or dehydration step of the manufacturing process, a small portion of the propylene glycol or other relatively low boiling solvents may evaporate together with the water. However, it has been found in the following examples that only about 0.5–2.0% of the propylene glycol is lost via evaporation during the dehydration step, and such solvent evaporation can be compensated for by the initial addition of 0.5–2.0% extra propylene glycol or other relatively low boiling polyhydric solvents at any stage of manufacture.

It should also be noted that the above-described dehydration step is unnecessary if one or more of the solvents and/or surfactants is added in anhydrous form (see Examples 3, 4, 7 and 10). Further, the dehydration step can be carried out at much lower temperatures by using a sealed reaction vessel at a pressure below atmospheric (under vacuum).

As well known in the art, the more volatile optional ingredients, such as dyes, fragrances and monohydric alcohols, should be added to the composition after cooling the molten composition, e.g., to 70° C. or below, so that the volatile components are not lost to evaporation.

The cleansing bars of the present invention can be manufactured by adding the soap in sodium salt form, or the fatty acid(s) can be added together with a sodium base, such as sodium hydroxide to form the soap in situ. As shown in the following examples, the moisturizing/cosmetics cleansing bars of the present invention have sufficient clarity to provide at least 85% light transmission, generally 85–95% light transmission. In accordance with another important feature of the present invention, when the bars are frozen and then thawed (Freeze/Thaw), the clarity remains at least 90%, preferably at least 95% of its original clarity compared to about 80% clarity after Freeze/Thaw of prior art bars containing 17.7% water (see Example 6—PREFERRED vs. Example 6—FORMED). The following examples show the compositions in percentages by weight of materials added to an agitated reaction vessel designated as "ADDED"; the composition formed from the materials added, designated "FORMED"; and the final composition after removal of water, if any, designated "FINAL":

In the following examples, when the soap is made in situ by reaction of fatty acid(s) with a caustic solution, e.g., NaOH, it is preferred to add the caustic solution before the addition of the fatty acid(s) to prevent formation of gels or lumps, which would increase manufacturing time. It has also been found that color degradation is minimized by adding any sorbitol only when the percent free fatty acid(s) is in the range of about 0.1% to about 2%, preferably in the range of 0.2% to 1.5%, more preferably in the range of 0.5% to 1.0% free fatty acid(s), based on the total weight of free fatty acids and neutralized fatty acids. The following is the preferred sequence of addition:

1—Mix the non-sorbitol polyhydric solvent(s), e.g., propylene glycol and glycerine and the surfactant(s);

2—Raise batch temperature to 70 to 80° C.;

3—Add less than the required amount of the caustic solution needed to fully neutralize the later-added fatty acids, e.g., about 95% of the required amount of caustic solution, e.g., NaOH;

4—Add the fatty acids, ensuring that the temperature remains above about 80° C. but below 100° C.;

5—Analyze for free tatty acid, e.g., titrate with NaOH, using a pH indicator, and adjust, if required, to 0.1 to 2.0% by weight, preferably 0.2 to 1.5% (most preferred 0.5% to 1.0%) based on the total weight of free fatty acids and neutralized fatty acids, as lauric acid, adding more caustic solution or more fatty acid, e.g., stearic acid;

6—Add the sorbitol solution, if sorbitol is one of the polyhydric solvents, and mix well;

7—Start the water evaporation step, e.g., by raising the temperature of the batch to about 99 to 102° C. with good agitation while preventing the batch from boiling. Of course, water removal under reduced pressure would require lower temperatures, the temperature depending upon the degree of applied vacuum;

8—When the desired amount of water has been removed, cool the batch to 75 to 80° C. Add the remaining caustic solution for complete neutralization of the fatty acids and any optional ingredients.

EXAMPLE 1

| | |
|---|---|
| ADDED | |
| Propylene Glycol | 22.8 |
| Glycerine | 15.3 |
| Sorbitol (70%) | 15.8 |
| Sorbitol (100%) | 0.0 |
| SLES (70%) | 12.0 |
| AOS* (40%) | 0.0 |
| FAE** (100%) | 0.0 |
| Myristic acid | 7.3 |
| Stearic acid | 11.1 |
| $H_2O$ | 9.9 |
| NaOH (50%) | 5.8 |
| TOTAL | 100.0 |
| FORMED | |
| Propylene Glycol | 22.8 |
| Glycerine | 15.3 |
| Sorbitol (100%) | 11.1 |
| SLES (100%) | 8.4 |
| AOS* (100%) | 0.0 |
| FAE** (100%) | 0.0 |
| NaMyristate | 8.0 |
| NaStearate | 12.0 |
| Total Water | 22.5 |
| TOTAL | 100.0 |
| CLARITY | 86/90 |
| MELTING POINT (° C.) | 50 |
| FINAL | |
| $H_2O$ Removed | 13.0 |

-continued

| | | |
|---|---|---|
| Propylene Glycol | 26.2 | Polyhydric Solvents: 54.5%<br>2-OH: 26.2%<br>$3^+$-OH: 28.3% |
| Glycerine | 17.6 | |
| Sorbitol | 12.7 | |
| SLES | 9.7 | |
| AOS* | 0.0 | |
| FAE** | 0.0 | |
| NaMyristate | 9.2 | |
| NaStearate | 13.8 | |
| Final Water | 10.9 | |
| TOTAL | 100.1 | |

*alpha olefin sulfonate
**fatty alcohol ethoxylate
CLARITY 84/90
MELTING POINT (° C.) 60

EXAMPLE 2

| Dry Sorbitol (no need to remove water) | | |
|---|---|---|
| ADDED | | |
| Propylene Glycol | 26.0 | |
| Glycerine | 17.0 | |
| Sorbitol (70%) | 0.0 | |
| Sorbitol (100%) | 13.7 | |
| SLES (70%) | 12.7 | |
| AOS* (40%) | 0.0 | |
| FAE** (100%) | 0.0 | |
| Myristic acid | 10.0 | |
| Stearic acid | 12.7 | |
| $H_2O$ | 0.0 | |
| NaOH (50%) | 7.3 | |
| TOTAL | 99.4 | |
| FORMED | | |
| Propylene Glycol | 26.0 | |
| Glycerine | 17.0 | |
| Sorbitol (100%) | 13.7 | |
| SLES (100%) | 8.9 | |
| AOS* (100%) | 0.0 | |
| FAE** (100%) | 0.0 | |
| NaMyristate | 11.0 | |
| NaStearate | 13.7 | |
| Total Water | 9.1 | |
| TOTAL | 99.4 | |
| FINAL | | |
| $H_2O$ Removed | 0 | |
| Propylene Glycol | 26.0 | Polyhydric Solvents: 56.7%<br>2-OH: 26.0%<br>$3^+$-OH: 30.7% |
| Glycerine | 17.0 | |
| Sorbitol | 13.7 | |
| SLES | 8.9 | |
| AOS* | 0.0 | |
| FAE** | 0.0 | 8.9 Surfactants |
| NaMyristate | 11.0 | |
| NaStearate | 13.7 | 24.7 Soap |
| Final Water | 9.1 | 9.1 Water |
| TOTAL | 99.4 | 99.4 Total |

*alpha olefin sulfonate
**fatty alcohol ethoxylate
CLARITY 85/90
MELTING POINT (° C.) 60

EXAMPLE 3

| High Level Of Surfactant | | |
|---|---|---|
| ADDED | | |
| Propylene Glycol | 20.4 | |
| Glycerine | 5.0 | |
| Sorbitol (70%) | 0.0 | |
| Sorbitol (100%) | 10.6 | |
| SLES (70%) | 13.4 | |
| AOS* (40%) | 0.0 | |
| FAE** (100%) | 25.0 | |
| Myristic acid | 8.5 | |
| Stearic acid | 10.8 | |
| $H_2O$ | 0.0 | |
| NaOH (50%) | 6.2 | |
| TOTAL | 99.9 | |
| FORMED | | |
| Propylene Glycol | 20.4 | |
| Glycerine | 5.0 | |
| Sorbitol (100%) | 10.6 | |
| SLES (100%) | 9.4 | |
| AOS* (100%) | 0.0 | |
| FAE** (100%) | 25.0 | |
| NaMyristate | 9.3 | |
| NaStearate | 11.7 | |
| Total Water | 8.5 | |
| TOTAL | 99.9 | |
| FINAL | | |
| $H_2O$ Removed | 0 | |
| Propylene Glycol | 20.4 | Polyhydric Solvents: 36.0%<br>2-OH: 20.4%<br>$3^+$-OH: 15.6% |
| Glycerine | 5.0 | |
| Sorbitol | 10.6 | |
| SLES | 9.4 | |
| AOS* | 0.0 | |
| FAE** | 25.0 | 34.4 Surfactants |
| NaMyristate | 9.3 | |
| NaStearate | 11.7 | 21.0 Soap |
| Final Water | 8.5 | 8.5 Water |
| TOTAL | 99.9 | 99.9 TOTAL |

*alpha olefin sulfonate
**fatty alcohol ethoxylate
CLARITY 82/90
MELTING POINT (° C.) 62

EXAMPLE 4

| Very Low Water Content, Low Foaming, Facial Cleanser | |
|---|---|
| ADDED | |
| Propylene Glycol | 26.1 |
| Glycerine | 17.2 |
| Sorbitol (70%) | 0.0 |
| Sorbitol (100%) | 12.6 |
| SLES (70%) | 0.0 |
| AOS* (40%) | 0.0 |
| FAE** (100%) | 12.4 |
| Myristic acid | 10.6 |
| Stearic acid | 13.4 |
| $H_2O$ | 0.0 |
| NaOH (50%) | 7.7 |
| TOTAL | 100.0 |
| FORMED | |
| Propylene Glycol | 26.1 |

-continued

| Very Low Water Content, Low Foaming, Facial Cleanser | | |
|---|---|---|
| Glycerine | 17.2 | |
| Sorbitol (100%) | 12.6 | |
| SLES (100%) | 0.0 | |
| AOS* (100%) | 0.0 | |
| FAE** (100%) | 12.4 | |
| NaMyristate | 11.6 | |
| NaStearate | 14.5 | |
| Total Water | 5.6 | |
| TOTAL | 100.0 | |
| FINAL | | |
| $H_2O$ Removed | 0 | |
| Propylene Glycol | 26.1 | Polyhydric Solvents: 55.9%<br>2-OH: 26.1%<br>$3^+$-OH: 29.8% |
| Glycerine | 17.2 | |
| Sorbitol | 12.6 | |
| SLES | 0.0 | |
| AOS* | 0.0 | |
| FAE** | 12.4 | 12.4 Surfactants |
| NaMyristate | 11.6 | |
| NaStearate | 14.5 | 26.1 Soap |
| Final Water | 5.6 | 5.6 Water |
| TOTAL | 100.0 | 100.0 TOTAL |

*alpha olefin sulfonate
**fatty alcohol ethoxylate
CLARITY 84/90
MELTING POINT (° C.) 62

EXAMPLE 5

| PEG-2ME | |
|---|---|
| ADDED | |
| Propylene Glycol | 16.4 |
| Glycerine | 0.0 |
| Sorbitol (70%) | 19.5 |
| Sorbitol (100%) | 0.0 |
| PEG-2ME* | 10.4 |
| SLES (70%) | 19.6 |
| AOS** (40%) | 0.0 |
| FAE*** (100%) | 0.0 |
| Myristic acid | 11.0 |
| Stearic acid | 14.1 |
| $H_2O$ | 0.0 |
| NaOH(50%) | 8.0 |
| Ethanol | 1.0 |
| TOTAL | 100.0 |
| FORMED | |
| Propylene Glycol | 16.4 |
| Glycerine | 0.0 |
| Sorbitol (100%) | 13.7 |
| PEG-2ME* | 10.4 |
| SLES (100%) | 13.7 |
| AOS** (100%) | 0.0 |
| FAE*** (100%) | 0.0 |
| NaMyristate | 12.1 |
| NaStearate | 15.2 |
| Ethanol | 1.0 |
| Total Water | 17.6 |
| TOTAL | 100.0 |

-continued

| PEG-2ME | | |
|---|---|---|
| FINAL | | |
| $H_2O$ Removed | 7.0 | |
| Propylene Glycol | 17.6 | Polyhydric Solvents: 43.5%<br>2-OH: 28.8%<br>$3^+$-OH: 14.7% |
| Glycerine | 0.0 | |
| Sorbitol | 14.7 | |
| PEG-2ME* | 11.2 | |
| SLES | 14.8 | |
| AOS** | 0.0 | |
| FAE*** | 0.0 | 14.8 Surfactants |
| NaMyristate | 13.0 | |
| NaStearate | 16.4 | 29.4 Soap |
| Ethanol | 1.0 | |
| Final Water | 11.3 | 11.3 Water |
| TOTAL | 100.0 | 100.0 TOTAL |

*polyethylene 2 glycol methyl ether
**alpha olefin sulfonate
***fatty alcohol ethoxylate
CLARITY 83/90
MELTING POINT (° C.) 62

EXAMPLE 6

| (Preferred Embodiment) | |
|---|---|
| ADDED | |
| Propylene Glycol | 25.1 |
| Glycerine | 6.0 |
| Sorbitol (70%) | 18.4 |
| Sorbitol (100%) | 0.0 |
| SLES (70%) | 18.4 |
| AOS* (40%) | 0.0 |
| FAE** (100%) | 0.0 |
| Myristic acid | 10.3 |
| Stearic acid | 13.1 |
| $H_2O$ | 1.2 |
| NaOH (50%) | 7.5 |
| TOTAL | 100.0 |
| FORMED | |
| Propylene Glycol | 25.1 |
| Glycerine | 6.0 |
| Sorbitol (100%) | 12.9 |
| SLES (100%) | 12.9 |
| AOS* (100%) | 0.0 |
| FAE** (100%) | 0.0 |
| NaMyristate | 11.3 |
| NaStearate | 14.2 |
| Total Water | 17.7 |
| TOTAL | 100.0 |

| | FINAL | | | | PREFERRED | | | | |
|---|---|---|---|---|---|---|---|---|---|
| $H_2O$ Removed | 5.0 | | | 7.5 | | | 10.0 | | |
| Propylene Glycol | 26.4 | Polyhydric | | 27.1 | Polyhydric | | 27.9 | Polyhydric | |
| | | Solvents: | 46.3% | | Solvents: | 47.5% | | Solvents: | 47.9% |
| | | 2-OH: | 26.4% | | 2-OH: | 27.1% | | 2-OH: | 27.9% |
| Glycerine | 6.3 | $3^+$-OH: | 19.9% | 6.5 | $3^+$-OH: | 20.4% | 6.7 | $3^+$-OH: | 20.0% |
| Sorbitol | 13.6 | | | 13.9 | | | 14.3 | | |
| SLES | 13.6 | | | 13.9 | | | 14.3 | | |
| AOS* | 0.0 | | | 0.0 | | | 0.0 | | |
| FAE** | 0.0 | | | 0.0 | | | 0.0 | | |
| NaMyristate | 11.9 | | | 12.2 | | | 12.5 | | |
| NaStearate | 14.9 | | | 15.3 | | | 15.7 | | |
| Final Water | 13.3 | | | 11.0 | | | 8.5 | | |
| TOTAL | 100.0 | | | 100.0 | | | 100.0 | | |

| FORMED | 0% $H_2O$ REMOVED | 5% $H_2O$ REMOVED | 7.5% $H_2O$ REMOVED | 10.0% $H_2O$ REMOVED |
|---|---|---|---|---|
| CLARITY | 85/90 | 83/90 | 81/90 | 79/90 |
| MELTING POINT (° C.) | 50 | 56 | 62 | 64 |
| HARDNESS (N) | 16.2 | | 22.5 | |
| Freeze/Thaw | 72/90 | | 78/80 | |
| Weight Loss | 10% | | 4% | |

*alpha olefin sulfonate
**fatty alcohol ethoxylate

EXAMPLE 7

| Dry Sorbitol (no need to remove water) | | |
|---|---|---|
| ADDED | | |
| Propylene Glycol | 27.1 | |
| Glycerine | 6.5 | |
| Sorbitol (70%) | 0.0 | |
| Sorbitol (100%) | 13.9 | |
| SLES (70%) | 18.6 | |
| AOS* (40%) | 0.0 | |
| FAE** (100%) | 0.0 | |
| Myristic acid | 11.3 | |
| Stearic acid | 14.4 | |
| $H_2O$ | 0.0 | |
| NaOH (50%) | 8.2 | |
| TOTAL | 100.0 | |
| FORMED | | |
| Propylene Glycol | 27.1 | |
| Glycerine | 6.5 | |
| Sorbitol (100%) | 13.9 | |
| SLES (100%) | 13.0 | |
| AOS* (100%) | 0.0 | |
| FAE** (100%) | 0.0 | |
| NaMyristate | 12.4 | |
| NaStearate | 15.6 | |
| Total Water | 11.5 | |
| TOTAL | 100.0 | |
| FINAL | | |
| $H_2O$ Removed | 0 | |
| Propylene Glycol | 27.1 | Polyhydric Solvents: 47.5%<br>2-OH: 27.1%<br>$3^+$-OH: 20.4% |

-continued

| Dry Sorbitol (no need to remove water) | | |
|---|---|---|
| Glycerine | 6.5 | |
| Sorbitol | 13.9 | |
| SLES | 13.0 | |
| AOS* | 0.0 | |
| FAE** | 0.0 | 13.0 Surfactants |
| NaMyristate | 12.4 | |
| NaStearate | 15.6 | 28.0 Soap |
| Final Water | 11.5 | 11.5 Water |
| TOTAL | 100.0 | 100.0 TOTAL |

*alpha olefin sulfonate
**fatty alcohol ethoxylate
CLARITY 81/90
MELTING POINT (° C.) 60

EXAMPLE 8

| | | |
|---|---|---|
| ADDED | | |
| Propylene Glycol | 24.3 | |
| Glycerine | 5.7 | |
| Sorbitol (70%) | 17.5 | |
| Sorbitol (100%) | 0.0 | |
| SLES (70%) | 14.3 | |
| AmphoAcetate (30%) | 8.6 | |
| FAE* (100%) | 0.0 | |
| Myristic acid | 9.9 | |
| Stearic acid | 12.6 | |
| $H_2O$ | 0.0 | |
| NaOH (50%) | 7.2 | |
| TOTAL | 100.1 | |
| FORMED | | |
| Propylene Glycol | 24.3 | |
| Glycerine | 5.7 | |
| Sorbitol (100%) | 12.3 | |
| SLES (100%) | 10.0 | |
| AmphoAcetate (100%) | 2.6 | |
| FAE* (100%) | 0.0 | |
| NaMyristate | 10.9 | |
| NaStearate | 13.6 | |
| Total Water | 20.8 | |
| TOTAL | 100.1 | |
| FINAL | | |
| $H_2O$ Removed | 9.0 | |
| Propylene Glycol | 26.7 | Polyhydric Solvents: 46.4%<br>2-OH: 26.7% |

-continued

| | | |
|---|---|---|
| | | 3⁺-OH: 19.8% |
| Glycerine | 6.3 | |
| Sorbitol | 13.5 | |
| SLES | 11.0 | |
| AmphoAcetate (100%) | 2.8 | |
| FAE* | 0.0 | 13.8 Surfactants |
| NaMyristate | 11.9 | |
| NaStearate | 15.0 | 26.9 Soap |
| Final Water | 12.9 | 12.9 Water |
| TOTAL | 100.1 | 100.1 TOTAL |

*fatty alcohol ethoxylate
CLARITY 81/90
MELTING POINT (° C.) 62

EXAMPLE 9

| | | |
|---|---|---|
| ADDED | | |
| Propylene Glycol | 22.4 | |
| Glycerine | 5.1 | |
| Sorbitol (70%) | 16.0 | |
| Sorbitol (100%) | 0.0 | |
| SLES (70%) | 0.0 | |
| AOS* (40%) | 29.4 | |
| FAE** (100%) | 0.0 | |
| Myristic acid | 9.0 | |
| Stearic acid | 11.5 | |
| $H_2O$ | 0.0 | |
| NaOH (50%) | 6.6 | |
| TOTAL | 100.0 | |
| FORMED | | |
| Propylene Glycol | 22.4 | |
| Glycerine | 5.1 | |
| Sorbitol (100%) | 11.2 | |
| SLES (100%) | 0.0 | |
| AOS* (100%) | 11.8 | |
| FAE** (100%) | 0.0 | |
| NaMyristate | 9.9 | |
| NaStearate | 12.4 | |
| Total Water | 27.2 | |
| TOTAL | 100.0 | |
| FINAL | | |
| $H_2O$ Removed | 18.0 | |
| Propylene Glycol | 27.3 | Polyhydric Solvents: 47.2%<br>2-OH: 27.3%<br>3⁺-OH: 19.9% |
| Glycerine | 6.2 | |
| Sorbitol | 13.7 | |
| SLES | 0.0 | |
| AOS* | 14.3 | |
| FAE** | 0.0 | |
| NaMyristate | 12.0 | |
| NaStearate | 15.2 | |
| Final Water | 11.2 | |
| TOTAL | 99.9 | |

*alpha olefin sulfonate
**fatty alcohol ethoxylate
CLARITY 81/90
MELTING POINT (° C.) 58

EXAMPLE 10

| High Soap Level - Added In Pellet Form (as Na salt) | | | |
|---|---|---|---|
| ADDED | | | |
| Propylene Glycol | 24.1 | | |
| Glycerine | 5.8 | | |
| Sorbitol (70%) | | | |
| Sorbitol (100%) | 12.6 | | |
| SLES (70%) | 17.0 | | |
| AOS* (40%) | 0.0 | | |
| Soap Pellets (75%)** | 10.0 | | |
| Myristic acid | 10.1 | | |
| Stearic acid | 13.0 | | |
| $H_2O$ | 0.0 | | |
| NaOH (50%) | 7.4 | | |
| TOTAL | 100.0 | | |
| FORMED | | | |
| Propylene Glycol | 24.1 | | |
| Glycerine | 6.5 | | |
| Sorbitol (100%) | 12.6 | | |
| SLES (100%) | 11.9 | | |
| AOS* (100%) | 0.0 | | |
| Soap | 7.5 | | |
| NaMyristate | 11.1 | | |
| NaStearate | 14.1 | | |
| Total Water | 12.0 | | |
| TOTAL | 99.7 | | |
| FINAL | | | |
| $H_2O$ Removed | 2.0 | | |
| Propylene Glycol | 24.6 | | |
| | | Polyhydric Solvents: | 44.1% |
| | | 2-OH: | 24.6% |
| Glycerine | 6.6 | 3⁺-OH: | 19.5% |
| Sorbitol | 12.9 | | |
| SLES | 12.1 | | |
| AOS* | 0.0 | 12.1 Surfactants | |
| FAE**** | 7.7 | | |
| NaMyristate | 11.3 | | |
| NaStearate | 14.3 | 33.3 | Soap |
| Final Water | 10.2 | 10.2 | Water |
| TOTAL | 99.7 | 99.7 | TOTAL |

*alpha olefin sulfonate
**$C_{12}$ 0.2%
$C_{14}$ 3.0%
$C_{16}$ 31.0%
$C_{18}$ 16.0%
$C_{18-1}$*** 45.0%
$C_{18-2}$*** 4.0%
$C_{18-3}$*** 1.0%
***fatty alcohol ethoxylate
****number of double bonds in $C_{18}$ acid
CLARITY 78/90
MELTING POINT (° C.) 62

What is claimed is:

1. A transparent, pour molded solid bar comprising, by weight:

15–65% water-soluble polyhydric solvents, including about 5% to about 35% having three or more hydroxyl groups, and about 10% to about 30% having two hydroxyl groups;

5–35% insoluble fatty acid soap;

5–40% surfactants; and

4–13% water.

2. The solid bar of claim 1, further including a monohydric alcohol in an amount of 4% by weight or less.

3. The solid bar of claim 1 comprising, by weight:

25–65% of said polyhydric solvents, including about 10% to about 30% having three or more hydroxyl groups, and about 15% to about 30% having two hydroxyl groups;

8–30% insoluble fatty acid soap;

5–30% surfactants; and

7–12% water.

4. The solid bar of claim 3, further including a monohydric alcohol in an amount 0.5–3%.

5. The solid bar of claim 3, comprising, by weight:

30–55% of said polyhydric solvents, including about 15% to about 25% having three or more hydroxyl groups, and about 20% to about 30% having two hydroxyl groups;

10–25% insoluble fatty acid soap;

8–25% surfactants; and

8–12% water.

6. The solid bar of claim 5, further including a monohydric alcohol in an amount of 0.5–2%.

7. The solid bar of claim 5, comprising, by weight:

35–50% of said polyhydric solvents, including about 17% to about 22% having three or more hydroxyl groups, and about 22% to about 27% having two hydroxyl groups;

10–15% insoluble fatty acid soap;

10–20% surfactants; and

10–12% water.

8. The solid bar of claim 7, further including a monohydric alcohol in an amount of 0.75–1.5%.

9. The solid bar of claim 1, wherein the soap is at least 90% selected from the group consisting of sodium myristate, sodium plamitate, sodium stearate, and mixtures thereof.

10. The solid bar of claim 9, wherein the soap is at least 95% by weight saturated.

11. The solid bar of claim 1, further including in a total concentration less than 20% by weight total, and less than 5% individually, additives selected from the group consisting of dyes, fragrances, antibacterial compounds, pH adjusters, thickeners, fillers, viscosity modifiers, buffering agents, foam stabilizers, antioxidants, foam enhancers, chelating agents, anti-microbial agents, preservatives, polymers, silicones, encapsulated materials, and mixtures thereof.

12. The solid bar of claim 9, wherein the soap contains an antibacterial compound that is triclocarban.

13. A method of making a transparent, pour molded bar comprising the steps of:

(a) mixing 15–65% by weight water-soluble polyhydric solvents, including about 5% to about 35% having three or more hydroxyl groups, and about 10% to about 30% having two hydroxyl groups;

5–40% by weight surfactants;

5–35% by weight insoluble fatty acid soap; and at least 4% by weight water, at a temperature sufficient to form a molten mixture;

(b) disposing the molten mixture in a shaped mold;

(c) dehydrating the molten mixture to 13% by weight water or less if the molten mixture contains more than 13% by weight water; and (d) allowing the molten mixture to cool and solidify to form said bar.

14. The method of claim 13, wherein at least one component of the bar selected from the group consisting of a water-soluble polyhydric solvent and a surfactant is added to the mixture in anhydrous form, such that the mixture is 13% by weight or less water, such that dehydrating the molten mixture is unnecessary.

15. The method of claim 13, wherein the soap is formed in situ by the addition of fatty acids and a base to form the sodium salt of the fatty acids.

16. The method of claim 13, wherein the water content of the molten mixture comprises greater than 13% to 30% by weight water, and the molten mixture is dehydrated before or after disposing the mixture in the shaped mold.

17. The method of claim 16, wherein the mixture comprises:

25–65% by weight of said polyhydric solvents, including about 10% to about 30% having three or more hydroxyl groups, and about 15% to bout 30% having two hydroxyl groups;

5–35% by weight insoluble fatty acid soap;

5–40% by weight surfactants; and more than 13% by weight water, and the method includes a dehydration step.

18. The method of claim 13, wherein the mixture comprises:

15–65% by weight of said polyhydric solvents;

5–35% by weight insoluble fatty acid soap;

5–40% by weight surfactants; and

4–13% by weight water, without a dehydration step.

19. The method of claim 17, wherein the molten mixture further includes a monohydric alcohol in an amount of 4% by weight or less.

20. The method of claim 17, wherein the water content of the mixture comprises more than 12% by weight water to about 30% by weight water, and the method includes a dehydration step.

21. The method of claim 13, wherein the mixtures comprises:

30–55% by weight of said polyhydric solvents, including about 15% to about 25% having three or more hydroxyl groups, and about 20% to about 30% having two hydroxyl groups;

8–30% by weight insoluble fatty acid soap;

5–30% by weight surfactants; and more than 13% by weight water, and the method includes a dehydration step.

22. The method of claim 13, wherein the mixture comprises:

35–50% by weight of said polyhydric solvents, including about 17% to about 22% having three or more hydroxyl groups, and about 22% to about 27% having two hydroxyl groups;

8–30% by weight insoluble fatty acid soap;

5–30% by weight surfactants; and

7–13% by weight water, without a dehydration step.

23. The method of claim 21, wherein the molten mixture includes a monohydric alcohol in an amount of 4% by weight or less.

24. The method of claim 17, wherein the water content of the mixture comprises more than 13% by weight water to about 30% by weight water, and the method includes a dehydration step.

25. The method of claim 23, wherein the amount of monohydric alcohol is 0.5% to about 3% by weight of the mixture.

26. The method of claim 13, wherein the mixture comprises:

30–55% of said polyhydric solvents, including about 15% to about 25% having three or more hydroxyl groups, and about 20% to about 30% having two hydroxyl groups;

10–25% insoluble fatty acid soap;

8–25% surfactants; and more than 13% by weight water, and the method includes a dehydration step.

27. The method of claim 26, wherein the mixture further includes 0.5–2% by weight of a monohydric alcohol.

28. The method of claim 13, wherein the mixture comprises:

40–55% by weight of said polyhydric solvents;

10–25% by weight insoluble fatty acid soap;

8–25% by weight surfactants; and

8–13% by weight water, without a dehydration step.

29. The method of claim 28, wherein the mixture includes a monohydric alcohol in an amount of 0.5–2% by weight.

30. The method of claim 13, wherein the mixture comprises:

35–50% of said polyhydric solvents;

10–15% insoluble fatty acid soap;

10–20% surfactants; and more than 13% by weight water, and the method includes a dehydration step.

31. The method of claim 13, wherein the mixtures comprises:

45–50% of said polyhydric solvents;

10–15% insoluble fatty acid soap;

10–20% surfactants; and

10–13% by weight water, without a dehydration step.

32. The method of claim 30, wherein the molten mixture includes a monohydric alcohol in an amount of 0.75–1.5% by weight.

33. The method of claim 13, wherein step (a) is performed in accordance with the following sequence of steps:

(1) mixing the non-sorbitol polyhydric solvents with the surfactants;

(2) heating the mixture to about 70 to 80° C.;

(3) adding an alkali to neutralize later-added fatty acid;

(4) adding the fatty acid;

(5) analyzing for free fatty acid;

(6) adjusting the amount of free fatty acid to the range of about 0.1% to about 2%, based on the total weight of free fatty acids, and neutralized fatty acids by the addition of more alkali or more fatty acid;

(7) adding sorbitol; and (8) adding sufficient caustic to neutralize the free fatty acids.

* * * * *